United States Patent
Nah et al.

(10) Patent No.: US 8,563,052 B2
(45) Date of Patent: Oct. 22, 2013

(54) METHOD FOR PREPARING GINTONIN, WHICH IS A NOVEL GLYCOLIPOPROETIN FROM PANAX GINSENG, AND GINTONIN, WHICH IS A NOVEL GLYCOLIPOPROTEIN, PREPARED BY THE METHOD

(75) Inventors: Seung Yeol Nah, Seoul (KR); Mi Kyung Pyo, Chungcheongbuk-do (KR); Sun Hye Choi, Seoul (KR); Byung Hwan Lee, Seoul (KR); Tae Joon Shin, Seoul (KR)

(73) Assignee: Konkuk University Industrial Cooperation Corp., Seoul (KR)

( * ) Notice: Subject to any disclaimer, the term of this patent is extended or adjusted under 35 U.S.C. 154(b) by 0 days.

(21) Appl. No.: 13/393,224

(22) PCT Filed: Aug. 12, 2010

(86) PCT No.: PCT/KR2010/005304
§ 371 (c)(1),
(2), (4) Date: Feb. 28, 2012

(87) PCT Pub. No.: WO2011/062354
PCT Pub. Date: May 26, 2011

(65) Prior Publication Data
US 2012/0165266 A1  Jun. 28, 2012

(30) Foreign Application Priority Data
Nov. 17, 2009 (KR) .................. 10-2009-0110662

(51) Int. Cl.
*A01N 65/00* (2009.01)
(52) U.S. Cl.
USPC ........................................ 424/725
(58) Field of Classification Search
None
See application file for complete search history.

(56) References Cited

FOREIGN PATENT DOCUMENTS

JP     02-045499 A  *  2/1990

* cited by examiner

*Primary Examiner* — Michael Meller
(74) *Attorney, Agent, or Firm* — Rabin & Berdo, P.C.

(57) ABSTRACT

Disclosed are the novel glycolipoprotein gintonin isolated and identified from ginseng, a method for preparing the same, and uses thereof. Gintonin causes a transient increase in intracellular free $Ca^{2+}$ level, which in turn activates endogenous $Ca^{2+}$-activated chloride channel to elevate intracellular calcium levels. Therefore, the novel glycolipoproteins are useful in the therapy and prophylaxis of calcium deficiency-associated diseases as well as effectively inducing calcium-dependent physiological activities, including adaptogenic activity, immunostimulatory activity, aphrodisiac activity, neuroprotection and neuroactivation, angiogenesis, and antidiabetic activity.

3 Claims, 12 Drawing Sheets

METHOD FOR PREPARING GINTONIN, WHICH IS A NOVEL GLYCOLIPOPROETIN FROM PANAX GINSENG, AND GINTONIN, WHICH IS A NOVEL GLYCOLIPOPROTEIN, PREPARED BY THE METHOD

TECHNICAL FIELD

The present invention relates to a novel glycolipoprotein present in ginseng. More particularly, the present invention relates to a novel glycolipoprotein isolated and characterized from ginseng and to a method for preparing a novel glycolipoprotein by isolating and characterizing it from gingseng, as well as the use of the novel glycolipoprotein.

BACKGROUND ART

Ginseng is known as an adaptogenic herb and has been taken orally as an adaptogen for many purposes, inter alia, for the prolongation of life. Traditionally, ginseng is used to enhance body functions against stress, fatigue, diseases, cancer and diabetes. Such a pharmaceutical belief has led people for hundreds of years in Korea, China and Japan to ingest ginseng. Currently, ginseng is one of the most famous and precious herbal medicines consumed around the world (Tyler, *J. Pharm. Technol.* 11, 214-220, 1995).

Ginsenosides the presence of which characterizes ginseng have typically been utilized in many physiological and pharmaceutical studies since they were first isolated and characterized in the early 1960s (Shibata, et al., Tetraheadron Letters No. 10, pp. 419-422, 1962). In addition, ginseng was also found to contain other ingredients including polysaccharides, polyacetylenes, and proteins (Nah, *Kor. J. Ginseng Sci.* 21, 1-12, 1997).

Ginsenosides are present in a small amount in ginseng and can be obtained by means of complicated isolation processes. Pure ginsenosides are highly expensive. For these reasons, a crude ginseng total saponin fraction (CGSF), which is obtained from ginseng roots by a butanol extraction method, is mostly employed for studies (Kanzaki, et al. *Br J Pharmacol.* 125(2), 255-262, 1998; Choi, et al. *Br J. Pharmacol.* 132, 641-648, 2001; Choi, et al., *J. Biol. Chem.* 276, 48797-48802, 2001; Choi, et al. *Eur J Pharmacol* 468, 83-92, 2003; Lee, et al, *J Biol Chem.* 279, 9912-9921, 2004; Jeong, et al, *Br J Pharmacol.* 142, 585-593, 2004; Reay, et al, *J Psychopharmacol.* 19, 357-365, 2005; Lee, et al, *Arch Pharm Res* 28, 413-420, 2005; Wei, et al *J Ethnopharmacol.* 111, 613-618, 2007; Eriksson, et al *J Ethnopharmacol.* 119, 17-23, 2008).

CGSF is found to take advantage of membrane signaling pathways when exerting its ginsenosidic activity. For example, Choi et al. demonstrated that ginsenoside treatment increased $Ca^{2+}$-activated chloride channel (CaCC) current through the signaling pathway that activates PTX-insensitive $G\alpha_{q/11}$ proteins coupled to PLCβ-IP3 in *Xenopus* oocytes (Choi, et al., *J. Biol. Chem.* 276, 48797-48802, 1 2001). Further, Lee et al. reported that CaCC currents produced by ginsenoside treatment diminished spontaneously after reaching peak amplitudes even in the continued presence of CGSF in *Xenopus* oocytes (Lee, et al, *J Biol Chem.* 279, 9912-9921, 2004).

Intraoocyte injection of calmodulin or depletion of intracellular calcium reservoirs inhibited CGSF-induced $Ca^{2+}$-activated CI-current activation (Lee, et al, *Arch Pharm Res* 28, 413-420, 2005). Further, studies revealed that CGSF treatment induced SOCE (stored-operated Ca2+ entry) in *Xenopus* oocytes (Jeong, et al, *Br J Pharmacol.* 142, 585-593, 2004), which caused an increase in extracellular or intracellular calcium level, allowing for the activation of CaCC in the *Xenopus* oocytes (Dascal, *CRC Crit Rev Biochem* 22, 317-387, 1987).

Surprisingly, the present inventors found that in the course of purifying ginsenosides from CGSF in order to confirm ginsenoside-induced CaCC activation, the induction of CGSF rapidly disappeared or was not obtained upon treatment with fractions which were more abundant in ginsenoside compared to CGSF, that is, ginsenosides purified from CGSF lacking the ability to induce CaCC activation in *Xenopus* oocyte, suggesting the presence of an unknown substance in CGSF, which has a major influence on CaCC activation in *Xenopus* oocytes.

Based on the finding, intensive and through research was made to isolate and identify the bioactive substance, culminating in the present invention.

DISCLOSURE

Technical Problem

It is therefore a primary object to provide a method for identifying a novel physiologically active, adaptogenic substance from ginseng, the novel physiologically active substance, and uses of the physiologically active substance.

Technical Solution

In order to accomplish the above objects, there is provided a method for isolating and identifying a novel glycolipoprotein from ginseng.

In detail, the method for preparing the novel glycolipoprotein (hereinafter referred to as "gintonin"), comprising: (1) providing a methanol extract from ginseng; (2) partitioning the methanol extract with a mixture of water and n-butanol; (3) fractionating the n-butanol layer into eight fractions by silica gel column chromatography with a mixture of chloromethane:methanol:water serving as an eluent; (4) subjecting a $7^{th}$ fraction to silica gel column chromatography eluting with a mixture of ethanol:ethyl acetate:water, to yield two sub-fractions, said $7^{th}$ fraction being identified as inducing the most activation of $Ca^{2+}$-activated Chloride Channel (CaCC); and (5) dializing fraction II to produce a final fraction, said fraction II being identified as inducing greater intracellular calcium release.

In addition, the method may further comprise (6) partitioning a solution of the final fraction in phosphate buffered saline, pH 7.2, containing NaCl into two sub-fractions by anion exchange chromatography and gel filtration chromatography; and (7) subjecting the two fractions to anion exchange chromatography eluting with Tris-HCl, pH 8.2, containing NaCl and with PBS, pH 7.2, containing NaCl, respectively, to separate individual glycolipoproteins.

In another aspect thereof, the present invention provides the novel glycolipoprotein isolated and identified from ginseng by the method.

The novel glycolipoprotein gintonin is characterized by being a pentamer with a molecular weight of 67 kDa and an apparent molecular weight of 13 kDa and having an amino acid composition comprising cysteine and cystine, asparagine and aspartic acid, glutamine and glutamic acid, serine, glycine, arginine, threonine, alanine, proline, valine, isoleucine, leucine, phenylalanine, tryptophan and lysine, a carbohydrate composition comprising rhamnose, arabinose, glucose, mannose, xylose and glucosamine, and a lipid composition comprising linoleic acid, palmitic acid, oleic acid and stearic acid.

Ginseng, belonging to the genus *Panax* of the family Araliaceae, may be available in various forms which are divided into fresh ginseng, white ginseng, and red ginseng, according to the processing method. Also, ginseng may be classified into artificially bred ginseng, artificially sown but wild-grown ginseng, and wild ginseng depending on the culturing conditions. As used herein, the term "ginseng" is meant to include all kinds of ginseng, so that American ginseng and Chinese ginseng as well as Korean ginseng fall within the scope of the present invention.

Below, a detailed description will be given of the present invention.

The novel glycolipoprotein, gintonin, found in ginseng can be obtained as follows.

Dried ginseng powder is subjected to extraction in about 1 to 20 volumes and preferably in about 1 to 10 volumes of a mixed solvent of 1:0.1 to 1:10 (v/v) water: lower alcohol of C1~C4, such as methanol, ethanol and/or butanol and preferably 1:0.2 to 1:5 (v/v) water:methanol with stirring, hot water, cold precipitation, heating, reflux condensation or ultrasonication, and preferably with reflux condensation, followed by filtration. This procedure is repeated many times and preferably two to five times. The filtrates thus obtained are pooled and concentrated at a reduced pressure, and the resulting concentrate is fractionated with a mixture of equal volumes of water and n-butanol to give a water fraction and an n-butanol fraction.

Of them, the n-butanol fraction, which corresponds to a crude ginseng total saponin fraction (CGSF), is subjected to silica gel column chromatography eluting with a mixture of chloromethane:methanol:water ($CHCl_3$:MeOH:$H_2O$) to yield eight fractions which are assayed for $Ca^{2+}$-activated Chloride Channel (CaCC) activation in *Xenopus* oocytes. The fraction which is evaluated to induce the highest activation is again fractionated by silica gel column chromatography eluting with a mixture of ethanol:ethylacetate:water (EtOH:EtOAC:$H_2O$) to give two sub-fractions. The one fraction with higher activity is dialyzed against excess water in a dialysis membrane to yield crude gintonin.

The crude gintonin according to the present invention is assayed for molecular weight by SDS-PAGE. Its protein and amino acid, and carbohydrate compositions are determined. Also, the lipid composition is analyzed using GC-MS.

From the crude gintonin, gintonins can be separated individually. In this regard, a solution of the crude gintonin in phosphate buffered saline (PBS) containing NaCl is subjected to anion exchange chromatography and gel filtration chromatography to produce two sub-fractions which are then further purified by anion exchange chromatography and eluted with Tris-HCl (pH 8.2) containing NaCl and PBS (pH 7.2) containing NaCl, respectively.

Gintonins according to the present invention may be sourced from various ginsengs including wild ginseng, artificially sown but wild-grown ginseng, artificially bred ginseng, American ginseng and Chinese ginseng as well as Korean ginseng. The ginseng used in the present invention may be in the form of fresh ginseng, white ginseng, and red ginseng and preferably in the form of Korean red ginseng (*Panax ginseng* C. A. Meyer) grown for four to six years.

In accordance with another aspect thereof, the present invention provides the use of the novel glycolipoprotein (gintonin) in the treatment and prevention of diseases associated with calcium deficiency.

In detail, the present invention provides a pharmaceutical composition for the prevention and treatment of diseases associated with calcium deficiency.

As shown by experiments with *Xenopus* oocytes, the gintonin in accordance with the present invention induces a transient increase in cytoplasmic free $Ca^{2+}$ level, which in turn activates endogenous CaCC to increase intracellular calcium levels. As a result, the gintonin is effectively applicable to the treatment and prevention of calcium deficiency-associated diseases, particularly, calcium signal dysfunction-associated nervous system diseases.

Examples of the calcium deficiency-associated diseases to which the gintonin of the present invention is applicable include schizophrenia, Alzheimer's disease, Huntington's disease, familial hemiplegic migraine, epilepsy episodic ataxia, and spinocerebellar ataxias, but are not limited thereto.

Further, the composition of the present invention is therapeutically effective for calcium deficiency-caused growth inhibition, and effectively induces various calcium-dependent physiological activities, such as adaptogenic activity, immunostimulatory activity, aphrodisiac activity, neuroprotection and neuroactivation, angiogenesis, and antidiabetic activity.

As ginseng has long been used as a source of herb medicines with safety, the gintonin of the present invention, isolated from ginseng, can be safely used without toxicity and side effects.

The pharmaceutical composition for the prevention and treatment of calcium deficiency-associated diseases in accordance with the present invention comprises gintonin in an amount of from 0.0001 to 10 wt %, preferably in an amount of from 0.001 to 1 wt %, based on the total weight thereof, as an active ingredient.

In addition, the gintonin-containing composition of the present invention may further comprise suitable carriers, excipients or diluents well-known in the pharmaceutical art. The dosage of gintonin of the present invention may be used alone or in combination with other pharmaceutically active compounds as well as in an appropriate assembly.

The pharmaceutical composition comprising gintonin in accordance with the present invention may be formulated into oral preparations such as powders, granules, tablets, capsules, suspensions, emulsions, syrups, aerosols, etc., or parenteral preparations such as external applications, suppositories and sterile injections. Among the carriers, diluents or excipients useful in the pharmaceutical composition are lactose, dextrose, sucrose, sorbitol, mannitol, xylitol, erythritol, maltitol, starch, acacia gum, aginate, gelatin, calcium phosphate, calcium silicate, cellulose, methyl cellulose, crystalline cellulose, polyvinyl pyrrolidone, water, methylhydroxybenzoate, propylhydroxybenzoate, talc, magnesium stearate and mineral oil. The active ingredient may be formulated in combination with a diluents or excipient such as a filler, a thickener, a binder, a wetting agent, a disintegrant, and/or a surfactant. Solid preparations intended for oral administration may take the form of tablets, pills, powders, granules, capsules, and the like. In regard to these solid agents, the active ingredient in the present invention is formulated in combination with at least one excipient such as starch, calcium carbonate, sucrose, lactose, or gelatin. In addition to such simple excipients, lubricants such as magnesium stearate and talc may be used. Liquid preparations intended for oral administration include suspensions, internal use solutions, emulsion, syrups, and the like. In addition to a simple diluent such as water or liquid paraffin, various excipients, such as wetting agents, sweetening agents, aromatics, preservatives, and the like may be contained in the liquid preparations. Also, the pharmaceutical composition of the present invention may be administered via a non-oral route. For this, sterile aqueous solutions, non-aqueous solvents, suspensions, emulsions, lyophilizates, suppositories, and the like may be used. Injectable propylene glycol, polyethylene glycol, vegetable oils such as olive oil, and esters such as ethyl oleate may be suitable for non-aqueous solvents and suspensions. The basic materials of suppositories include Witepsol, macrogol, Tween 61, cacao butter, laurin butter, and glycerogelatin.

The dosage of the composition of the present invention may vary depending on various factors including the patient's condition and weight, the severity of disease, dosage form, the route of administration and the time of administration, and can be suitably determined by the attending physician. To achieve the desired effects, however, the composition of the present invention may be preferably administered at a daily dose of from 0.0001 to 100 mg/kg. The composition may be administered in a single dose per day or in multiple doses per day. The dosage is not intended to limit the present invention in any way.

The pharmaceutical composition of the present invention may be administered to mammals such as rats, mice, livestock, and humans, via various routes. All routes of administration may be expected, for example, oral or intrarectal administration or intravenous, intramuscular, subcutaneous, intradural, or intracerebroventricular injection may be contemplated.

The composition comprising gintonin in accordance with the present invention may be applied to medicaments, foods and beverages for use in the prevention and treatment of calcium deficiency-associated diseases. For example, the gintonin may be added to various foods, beverages, gums, teas, vitamin complexes, health functional foods, etc.

Being almost free of toxicity and side effects, the gintonin of the present invention can be safely ingested for a long period of time for preventive purposes.

When added to foods or beverages to prevent calcium deficiency-associated diseases, the amount of the gintonin used may be from 0.01 to 15 wt % based on the total weight of the food or beverage. For a health beverage, the gintonin of the present invention may be added in an amount of from 0.02 to 5 g per 100 ml and preferably in an amount of from 0.3 to 1 g per 100 ml.

No particular limitations are imparted to the other components of the health beverage composition so long as the gintonin of the present invention is used in an amount such as the one described above. Like conventional beverages, the health beverage of the present invention may further comprise various flavor modifiers or natural carbohydrates. Examples of the natural carbohydrates useful in the present invention include monosaccharides such as glucose, fructose, etc.; disaccharides such as maltose, sucrose, etc.; polysaccharides such as dextrin, cyclodextrin, etc.; and sugar alcohols such as xylitol, sorbitol, erythritol, etc. As for the flavor modifiers, they are advantageously natural flavor modifiers (taumatin, stebia extracts, i.e, Rebaudioside A, glycyrrhizin), and synthetic sweeteners (saccharin, aspartame, etc.). The amount of the natural carbohydrates used may be from 1 to 20 g and preferably from to 12 g per 100 ml of the health beverage composition of the present invention.

In addition, the composition of the present invention may be supplemented with a variety of agents including nutrients, vitamins, minerals (electrolytes), flavoring agents, synthetic and/or natural, colorants, thickeners (cheese, chocolate), pectic acid or salts thereof, alginic acid or salts thereof, organic acids, protective colloidal thickening agents, pH modifiers, stabilizers, preservatives, glycerin, alcohols, carbonating agents used in carbonated beverages, etc. For use in the preparation of fruit or vegetable juices, the composition of the present invention may further comprise fresh fruit and/or vegetable soup. These components may be used separately or in combination. As a rule, the amount of the agents ranges from zero to 20 parts by weight per 100 weight parts of the composition.

Advantageous Effects

As described hitherto, the present invention provides a method for preparing gintonin, a family of novel glycolipoproteins, by means of isolation and identification from ginseng, the novel glycolipoproteins prepared using the method, and uses of the novel glycolipoprotein gintonin in the prevention and treatment of calcium deficiency-associated diseases.

The function of the gintonin according to the present invention is to induce a transient increase in cytoplasmic free $Ca^{2+}$ level, which in turn activates endogenous CaCC, as measured in *Xenopus* oocytes, whereby the gintonin according to the present invention can be useful in the prevention and treatment of calcium deficiency.

Further, the gintonin of the present invention can potently induce various calcium-dependent physiological activities, such as adaptogenic activity, immunostimulatory activity, aphrodisiac activity, neuroprotection and neuroactivation, angiogenesis, and antidiabetic activity.

DESCRIPTION OF DRAWINGS

FIG. 12(C) shows the effects of active or inactive PLC inhibitors on gintonin-mediated increase in cytoplasmic $[Ca^{2+}]_i$ in EAT cells in $Ca^{2+}$ buffer (1.5 mM $Ca^{2+}$) and in $Ca^{2+}$ free buffer (0.2 mM EGTA). Pretreatment of active PLC inhibitor (U73122, 10 μM) but not inactive PLC inhibitor (U73343, 10 μM) blocked gintonin (100 ng/mL)-mediated elevation of $[Ca^{2+}]_i$ in $Ca^{2+}$ and $Ca^{2+}$ free buffer (0.2 mM EGTA). Data are represented as means ±SEM (n=4-5/group).

BEST MODE

A better understanding of the present invention may be obtained through the following examples which are set forth to illustrate, but are not to be construed as limiting the present invention.

Example 1

Separation of Crude Gintonin from Ginseng

After being crushed into small pieces (>3 mm), 20 kg of 6-year-old red ginseng (*Panax ginseng* C. A. Meyer), purchased from Korea Ginseng Corp. (Daejeon, Korea), was extracted in 30 liters of 80% methanol at 80° C. by reflux condensation, followed by filtration in a vacuum. This procedure was repeated three times. The extracts thus obtained were pooled and concentrated at a reduced pressure (the methanol extract amounted to a total of 6.2 kg). The concentrate was fractionated with a mixture of solvent and n-butanol (1:1) to yield respective fractions of water and n-butanol (the n-butanol fraction totaled 908 g).

Figure 1:
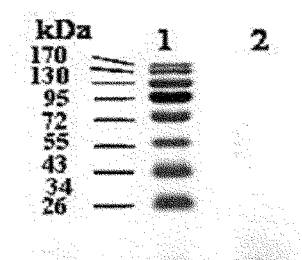
FIG. 1A is a process scheme illustrating the isolation and identification of the novel glycolipoprotein gintonin.
FIG. 1B is a chromatogram showing the ability of the gintonin fraction to induce CaCC activation.
FIG. 1C shows SDA-PAGE results of crude gintonin.
Figure 2:
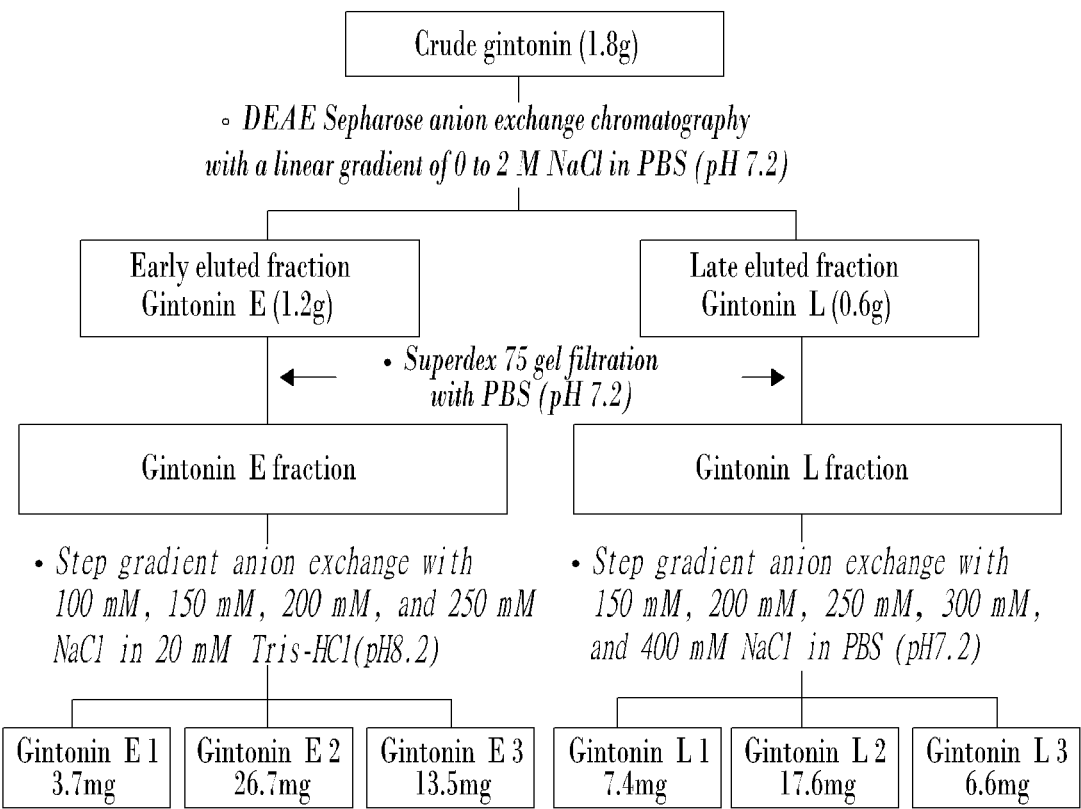
FIG. 2 is a process scheme illustrating the separation of crude gintonin into individual gintonins.

The n-butanol fraction (crude ginseng total saponin fraction, CGSF) was further concentrated and subjected to silica gel column chromatography with a mixture of chloroform:methanol:water ($CHCl_3$:MeOH:H2O=13:7:2) as the eluent to yield 8 sub-fractions which were then assayed for activity of inducing the activation of endogenous ($Ca^{2+}$-activated Chloride Channel (CaCC) in *Xenopus* oocytes. Sub-fraction 7, which was found to show the highest activity (see FIG. 1B), was fractionated again with a mixture of ethyl acetate:ethanol:water (EtOAc:EtOH:$H_2O$=1:3:0.5) by silica gel column chromatography to yield two fractions.

The two fractions were assayed for ability to induce intracellular calcium release in EAT (Ehrlich Ascites Tumor) cells and CaCC activation in *Xenopus* oocytes. Fraction II with higher activity was dialyzed against excess distilled water (DW) at 4° C. for hours with Spectra/Por dialysis bag (molecular weight cut off 6,000~8,000 Da) (Spectrum Laboratories, Inc., California, USA) to remove ginsenosides and other small molecular weight compounds.

The dialysate thus obtained was found to have an apparent molecular of about 13 kDa as measured by SDS-PAGE using Coomassie Brilliant Blue, suggesting that the substance of fraction II which is responsible for inducing intracellular calcium release in EAT cells and CaCC activation in *Xenopus* oocytes should be a kind of proteins other than ginsenosides. Thus, these putative proteins were designated gintonins. The final fraction was designated crude gintonin.

In contrast, the water fractions containing proteins and polysaccharides and the petroleum ether fraction containing lipids were observed to have no influence on intracellular calcium release in EAT cells nor CaCC activation in *Xenopus* oocytes (data not shown).

Example 2

Separation of Individual Gintonins

In order to separate individual gintonins therefrom, the crude gintonin obtained in Example 1 was dissolved in phosphate buffered saline (PBS) (pH 7.2) and purified using anion exchange chromatography (GE Healthcare, Uppsala, Sweden) equipped with DEAE sepharose CL06B column to yield two major peaks. The eluent with a linear gradient of from 0 to 2 M NaCl in PBS was allowed to flow at a rate of 1 ml/min with monitoring at 280 nm. The two major peaks were designated gintonin E (early eluted gintonin) and gintonin L (late eluted gintonin), respectively.

Figure 3:
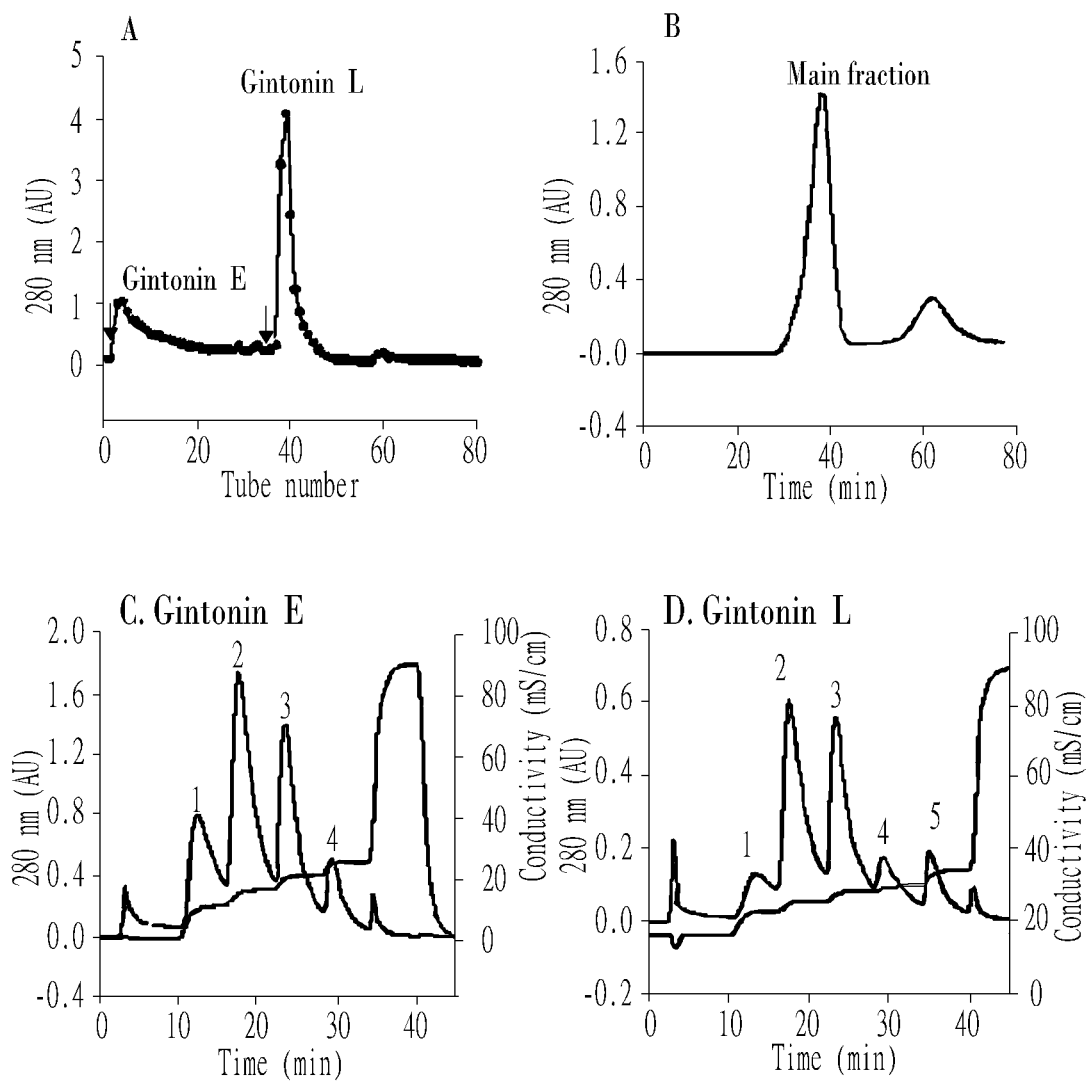
FIG. 3 shows the separation of gintonins E and L from crude gintonin by anion exchange chromatography (A) and provides a gel filtration chromatogram of the gintonin L fraction (B) and anion exchange chromatograms of the gintonin E (C) and gintonin L (D).

After being concentrated using a CentriVap DNA vacuum concentrator (Labconco, Mo., USA), gintonins E and L were loaded into Superdex 75 gel filtration columns and eluted with PBS (pH 7.2) at a flow rate of 0.5 ml/min and were monitored at 280 nm. A major peak corresponding to a large molecular weight and a minor peak were identified (see FIG. 3B).

Gintonins E and L were identified as inducing CaCC activation in *Xenopus* oocytes. The gintonin E fraction was again loaded into a DEAE anion exchange column (HiTrap™ DEAE FF, 1 ml) eluting with a step gradient of 100, 150, 200 and 250 mM NaCl in 20 mM Tris-HCl (pH 8.2) at a flow rate of 1 ml/min to yield four peaks (see FIG. 3C). The fractions of the respective 100, 150 and 200 mM NaCl eluent were concentrated by extensive dialysis and subjected to DEAE anion exchange chromatography with a step gradient of 0 to 1 M NaCl in 20 mM Tris-HCl (pH 8.2), followed by Superdex 75 gel filtration chromatography to produce final fractions in an amount of 3.7, 26.7 and 13.5 mg, respectively, which are designated gintonin L1, L2 and L3.

On the basis of 908 g of the CGSF, the purification yield was calculated to be 0.0004% (3.7 mg) for gintonin E1, 0.0029% (26.7 mg) for gintonin E2, 0.0015% (13.5 mg) for gintonin E3, 0.0008% (7.4 mg) for gintonin L1, 0.0019% (17.6 mg) for gintonin L2, and 0.007% (6.6 mg) for gintonin L3.

Example 3

Determination of Molecular Weight of Gintonins

Molecular weights of the six different gintonins were determined by the Yamamoto method (Yamamoto, Y., Nunome, T., Yamauchi, R., Kato, K., and Sone, Y. (1995)

Carbohydr Res. 275, 319-332) using gel filtration chromatography. In this regard, an eluent was passed at a flow rate of 0.5 ml/min through a BioLogic DuoFlow™ chromatography system (BIO-RAD, California, USA) having a Superdex 75 column (10×300 mm) equilibrated with PBS (pH 7.2) under monitoring at 280 nm. The molecular weights of the eluates were determined using a calibration curve constructed with standard proteins such as immunoglobulin G (IgG; 160,000 Da), bovine serum albumin (BSA; 67,000 Da), β-lactoglobulin (35,000 Da), cytochrome C (12,327 Da), and aprotinin (6,512 Da).

Figure 4:
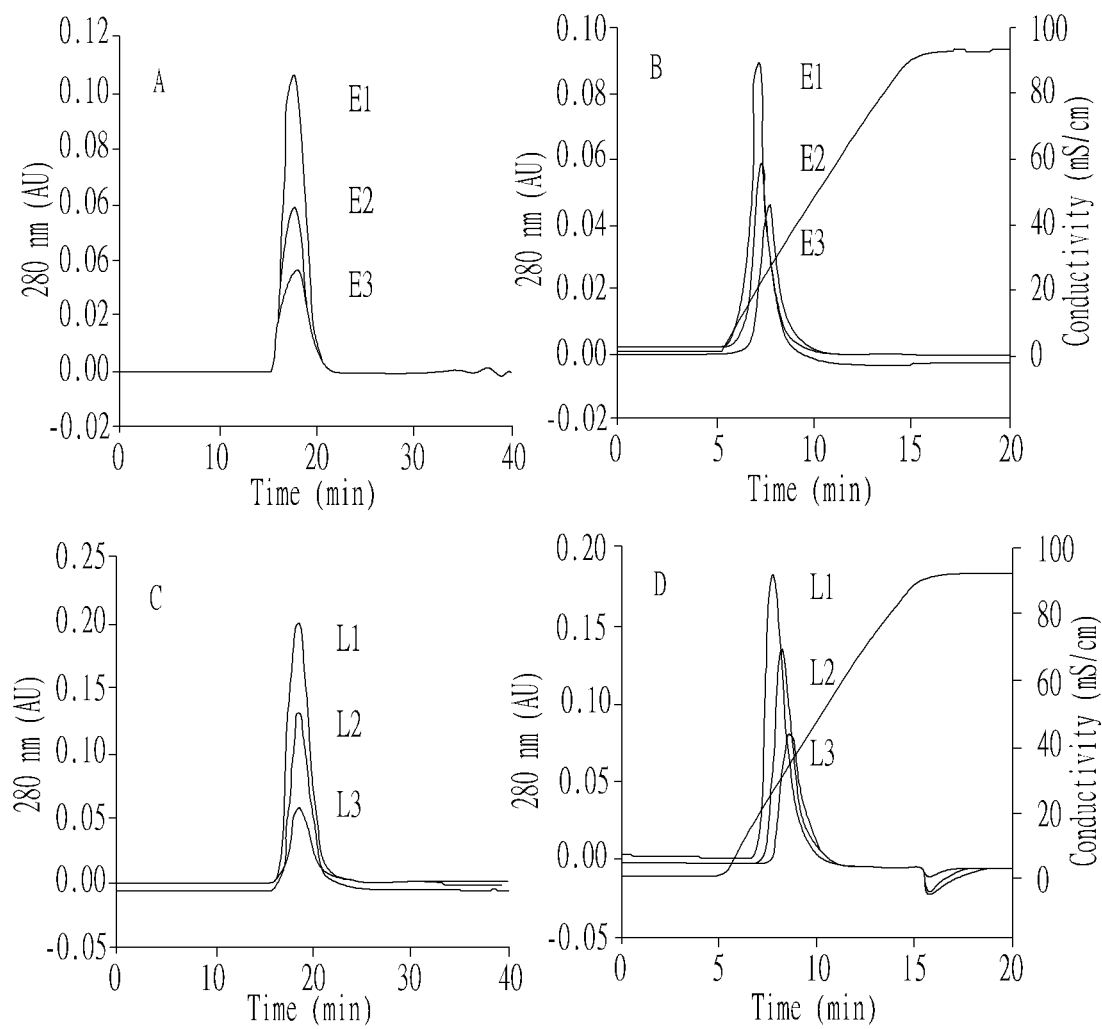
FIG. 4 shows elution patterns of individual gintonins by gel chromatography or continuous anion exchange chromatography in the form of an overlay of gel filtration chromatograms of purified gintonin E1~E3, and L1~L3 (A, C) and in the form of an overlay of anion exchange chromatograms of purified gintonin E1~E3 and L1~L3 (B, D).

Gintonins were observed to have almost the same molecular weights as they were eluted almost at the same time by gel filtration chromatography although they had a different elution pattern depending on the NaCl gradient due to their different charges (see FIGS. 4B and 4D).

Figure 5:
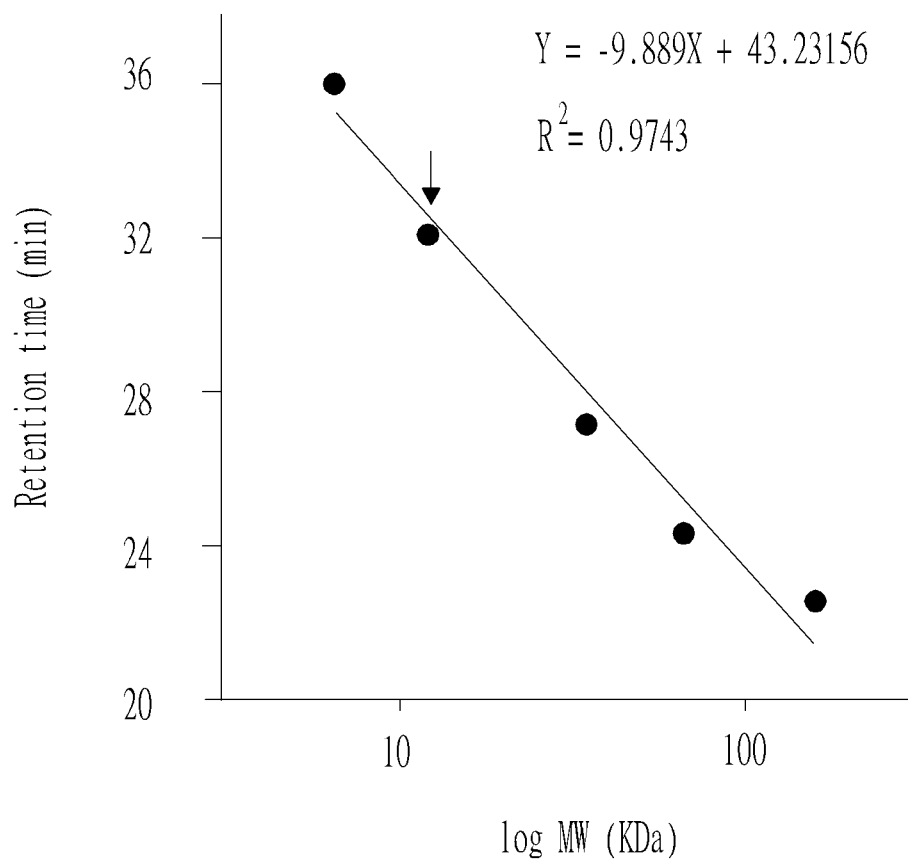
FIG. 5 is a calibration curve for determining the molecular weight of gintonins through gel filtration chromatography in which each point represents the standard protein that was used (IgG: 160 kDa; BSA: 67 kDa; β-lactoglobulin: 35 kDa; cytochrome C: 12 kDa; aprotinin: 6.5 kDa), with the arrow indicating gintonin.

The standard curve measured the native molecular weight of gintonin L2 at about 67 kDa (see FIG. 5) and also detected about 67 kDa for other gintonins (data not shown).

The six gintonins were read as a single major band, although broad, on SDS-PAGE, with an apparent molecular weight of about 13 kDa.

Figure 6:
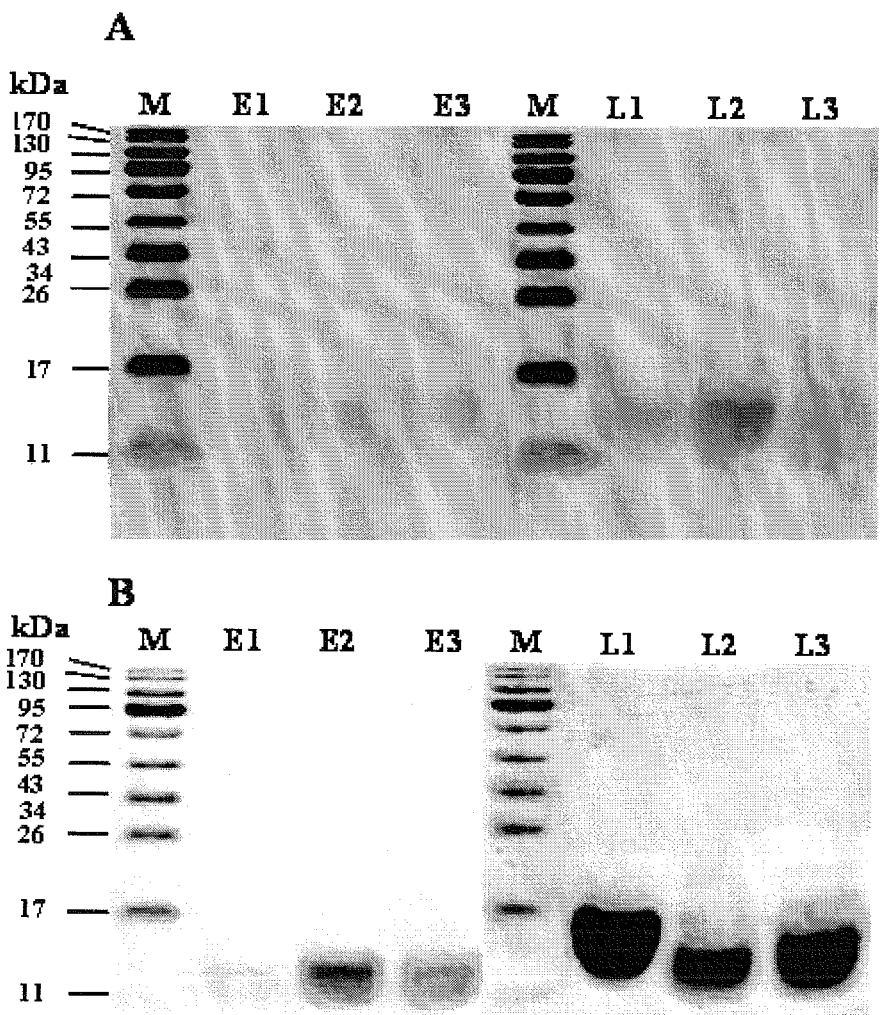
FIG. 6 shows the determination of molecular weight of gintonin through SDS-PAGE (A) and the retention of carbohydrates within the individual gintonins in gel staining SDS-PAGE (B).

These data indicate that the gintonins of the present invention are pentamers (see FIG. 6A).

Example 4

Determination of Purity of Gintonin

In order to determine purities of the crude gintonin and the individual gintonins, SDS-PAGE was performed on 12.0% separating gel (Laemmli, U. K. (1970) Nature 227, 680-685).

In detail, 100 μg of each of the crude gintonin and the individual gintonins E1~E3 and L1~L3 were loaded onto a lane and run in the presence of an electric field after which the gintonin bands were visualized with Coomassie Brilliant Blue R-250. For glycoprotein detection, the gel was stained by PAS (periodic acid—Schiff) staining, incubated for 30 min in a 4% ethanol-7% acetic acid solution and then for one hour in a 1% periodic acid-3% acetic acid solution. The periodic acid solution was removed and Schiff's reagent was added and incubated for one hour. Bands of stained glycoproteins developed a pink color and the PAS-stained gels were soaked for one hour in 7.5% acetic acid before storage.

Example 5

Analysis of Gintonins for Amino Acid Composition

For general amino acid analysis, 30 μg of gintonin was hydrolyzed in vacuo at 110° C. for 24 hours in the presence of 6 N HCl. For cysteine analysis, gintonin was subjected to peroxidation and then hydrolyzed at 110° C. for 24 hours in the presence of 6 N HCl before treatment with a mixture of formic acid:peroxide (10:1). Tryptophan analysis was performed by hydrolyzing samples with 4 M methanesulfonic acid and adding 4 M KOH.

Amino acids derivatized with phenylisothiocyanate (PITOC) were quantified by HPLC (Hewlett Packard 1100 series) using Waters Nova-Pak C18 column (3.9×300 mm) in the Korea Basic Science Institute, located in Daejeon, Korea.

Protein concentrations were determined by the Bradford assay (Bradford, M. M. (1976). Anal. Biochem. 72, 248-254) using bovine serum albumin (BSA) as a standard.

Example 6

Partial Amino Acid Sequence of Gintonin

The N-terminal amino acid sequence of gintonin was determined by automated Edman degradation on a gas-phase protein sequencer (Applied Biosystem model 477A) and on a MilliGen 6600 solid-phase sequencer.

By SDS-PAGE, 100 μg of gintonin was separated on 12% separating gel, followed by visualization of protein bands with Coomassie Brilliant Blue R-250. The bands were excised and subjected to in-gel digestion with trypsin and the digests were desalted and concentrated. All mass spectrometer (MS/MS) of peptides generated by the in-gel digestion was performed by nano-electrospray ionization on an MS (QTOF II; Micromass, UK) at the Korea Basic Science Institute. Product ions were analyzed using an orthogonal time-of-flight (TOF) analyzer fitted with a reflector, a microchannel plate detector, and a time-to-digital converter. The data were processed using a personal computer running Mass Lynx software on the Window NT environment. The sequence homologues were searched for using the BLAST program (http://www.ncbi.nlm.nih.gov/BLAST.cgi).

Table 1 summarizes the de novo amino acid sequences and compositions of gintonins. Purified gintonins were subjected to N-terminal amino acid sequencing by automated Edman degradation. Full amino acid sequences of gintonin could not be obtained because of N-terminal blocking. Eighteen internal peptide sequences which were obtained from trypsinized gintonins using MALDI-TOF-MS/MS allowed the inference to be made that each of six gintonins generally has several peptides with a partial homology with human glucokinase and glucokinase isoform 2 (data not shown).

The contents of total protein in gintonins were determined to be about 9.4% for gintonin E1, 24.1% for E2, 20.5% for E3, 35.8% for L1, 37.1% for L2, and 39.6% for gintonin L3 as measured by the Bradford method. Thus, the protein contents of gintonin L1-L3 are about three times higher than those of gintonin E1.

In addition, gintonins are more abundant in hydrophobic amino acids than hydrophilic amino acids, with no detection of histidine (His), tyrosine (Tyr) and methionine (Met). The N-terminal blocking was inferred to be responsible for the failure to detect Met.

Gintonins E1~E3 and L1~L3 had the highest contents of phenylalanine in common. Higher contents of lysine (Lys) were detected in gintonins E1~E3 than in gintonins L1~L3 (see Table 1).

TABLE 1

| Amino acid composition of gintonins (%) | | | | | | |
|---|---|---|---|---|---|---|
| Amino acid | E1 | E2 | E3 | L1 | L2 | L3 |
| CYA | 2.90 | 3.87 | 1.29 | 0.97 | 1.14 | 0.94 |
| ASX | 8.27 | 8.60 | 6.11 | 1.89 | 3.71 | 3.98 |
| GLX | 6.67 | 7.22 | 4.57 | 2.43 | 4.89 | 4.25 |
| Ser | 4.57 | 4.29 | 3.29 | 2.29 | 5.00 | 3.59 |
| Gly | 12.40 | 13.67 | 11.55 | 12.88 | 11.57 | 10.56 |
| His | 0.00 | 0.00 | 0.00 | 0.00 | 0.00 | 0.00 |
| Arg | 1.68 | 1.85 | 1.19 | 0.63 | 1.69 | 1.10 |
| Thr | 3.11 | 3.29 | 2.20 | 1.37 | 1.46 | 1.79 |
| Ala | 5.62 | 6.98 | 3.59 | 4.52 | 4.07 | 4.67 |
| Pro | 4.52 | 4.90 | 3.30 | 3.18 | 3.09 | 4.86 |
| Tyr | 0.00 | 0.00 | 0.00 | 0.00 | 0.00 | 0.00 |
| Val | 3.13 | 3.89 | 3.74 | 3.99 | 4.68 | 6.00 |
| Met | 0.00 | 0.00 | 0.00 | 0.00 | 0.00 | 0.00 |
| Ile | 6.03 | 5.16 | 7.54 | 10.36 | 8.83 | 7.76 |
| Leu | 3.96 | 5.09 | 3.43 | 4.26 | 6.83 | 10.09 |

TABLE 1-continued

Amino acid composition of gintonins (%)

| Amino acid | E1 | E2 | E3 | L1 | L2 | L3 |
|---|---|---|---|---|---|---|
| Phe | 26.40 | 18.66 | 35.10 | 28.89 | 21.37 | 22.47 |
| Trp | 3.59 | 7.10 | 3.62 | 4.88 | 8.13 | 6.10 |
| Lys | 7.14 | 5.42 | 9.78 | 17.48 | 13.56 | 11.85 |

CYA, the sum of cysteine and cystine; ASX, the sum of asparagines and aspartic acid, GLX, the sum of glutamine and glutamic acid.

Example 7

Analysis for Carbohydrate Composition of Gintonin

There is a possibility that gintonin might contain carbohydrate moieties since the bands of individual gintonins from SDS-PAGE appeared single but broad and were not strongly stained with Coomassie brilliant blue, as shown in FIG. 6A.

To examine carbohydrate compositions of gintonins, therefore, individual gintonins in glass ampules were hydrolyzed in 2 M trifluoroacetic acid for four hours at 100° C. to detect neutral sugars, and were hydrolyzed in 6 N HCl for four hours at 100° C. to detect amino sugars and acid sugars.

Carbohydrate compositions of gintonins were analyzed by a high performance anion exchange chromatography-pulsed ampherometric detection system (HPAEC-PAD system; Dionex, Sunnyvale, Calif., USA) with a CarboPac™ PA1 column at the Carbohydrate Bioproduct Research Center, Sejong University (Seoul, Korea) after PAS (periodic acid—schiff based staining). The molar ratios of monosaccharides were calculated from peak areas. The carbohydrate contents were also determined by phenol-sulfuric acid method for neutral sugars and the anthrone method for acid sugars (Scott, T. A., and Melvin, E. H. (1953) *Anal. Biochem.* 25, 1656-1660).

Figure 7:
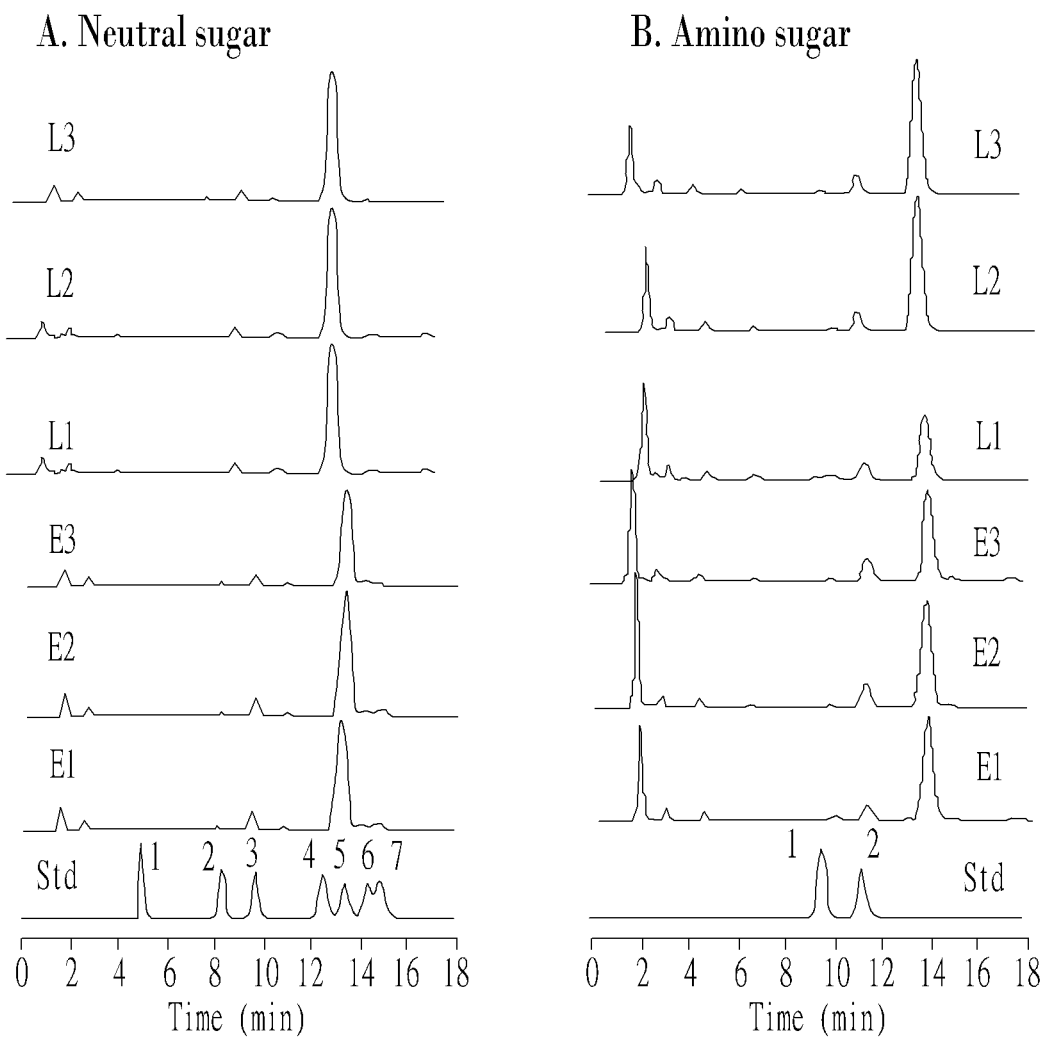
FIG. 7 is of HPAED-PAD chromatograms showing carbohydrate compositions of the individual gintonins for neutral sugars (standard material: 1. L-fructose, 2. L-rhamnose; 3. D-arabinose; 4. D-galactose; 5. D-glucose; 6. D-mannose; 7. D-xylose) (A) and for amino sugars (standard material: 1. D-galactosamine; 2. D-glucosamine) (B).

From the data obtained, gintonins were found to comprise the five different neutral sugars rhamnose, arabinose, glucose, mannose, and xylose, and the one amino sugar glucosamine and carbohydrate compositions of six gintonins were almost similar to each other (see Table 2 and FIG. 7). Mannose was not detected in gintonins E1~E3.

Acidic sugars such as 1-N-acetyl-neuramic acid, 2-galactouronic acid, and 3-glucouronic acid were not detected in any of the gintonins (data not shown).

Finally, the content of total carbohydrate in gintonins were about 34.3% for gintonin E1, 45.3% for E2, 38.1% for E3, 36.0% for L1, 29.8% for L2, and 45.2% for L3. The above results again confirmed that gintonins are glycoproteins.

TABLE 2

Carbohydrate composition of gintonins

| Carbohydrate | E1 | E2 | E3 | L1 | L2 | L3 |
|---|---|---|---|---|---|---|
| Rhamnose | 0.86 | 1.02 | 0.91 | 1.11 | 0.93 | 1.09 |
| Arabinose | 5.66 | 5.10 | 5.66 | 9.11 | 8.32 | 7.36 |
| Glucose | 84.84 | 84.41 | 83.97 | 77.16 | 74.64 | 71.59 |
| Manose | — | — | — | 1.76 | 2.30 | 3.37 |
| Xylose | 1.12 | 0.94 | 0.95 | 2.73 | 2.55 | 2.50 |
| Glucosamine | 7.52 | 8.53 | 8.51 | 8.13 | 11.26 | 14.09 |

Example 8

Lipid Composition Analysis of Gintonins

Since gintonins were co-fractionated with ginsenosides by butanol extraction, there was the possibility that gintonin also contained lipid moieties.

To confirm lipid and hydrophobic moieties, individual gintonins were hydrolyzed in 6 N HCl for four hours at 100° C. or digested by lipoprotein lipase.

In this context, acid hydrolysates or digests of CGSF were concentrated and further partitioned between distilled water and n-hexane. The n-hexane layer was prepared for lipid and hydrophobic moiety analysis by an Agilent 6890N GC-MS system (Agilent Technologies, Palo Alto, Calif., USA) with a DB5-MS capillary column (30 cm×250 μm×0.25 μm) at the Korea Basic Science Institute and by a GC (Agilent 6890N) equipped with flame ionization detector and a split injection system and fitted with a supelco SPB-1 capillary column (15 m×0.32 mm inside diameter, 0.25 mm thickness).

Figure 8:
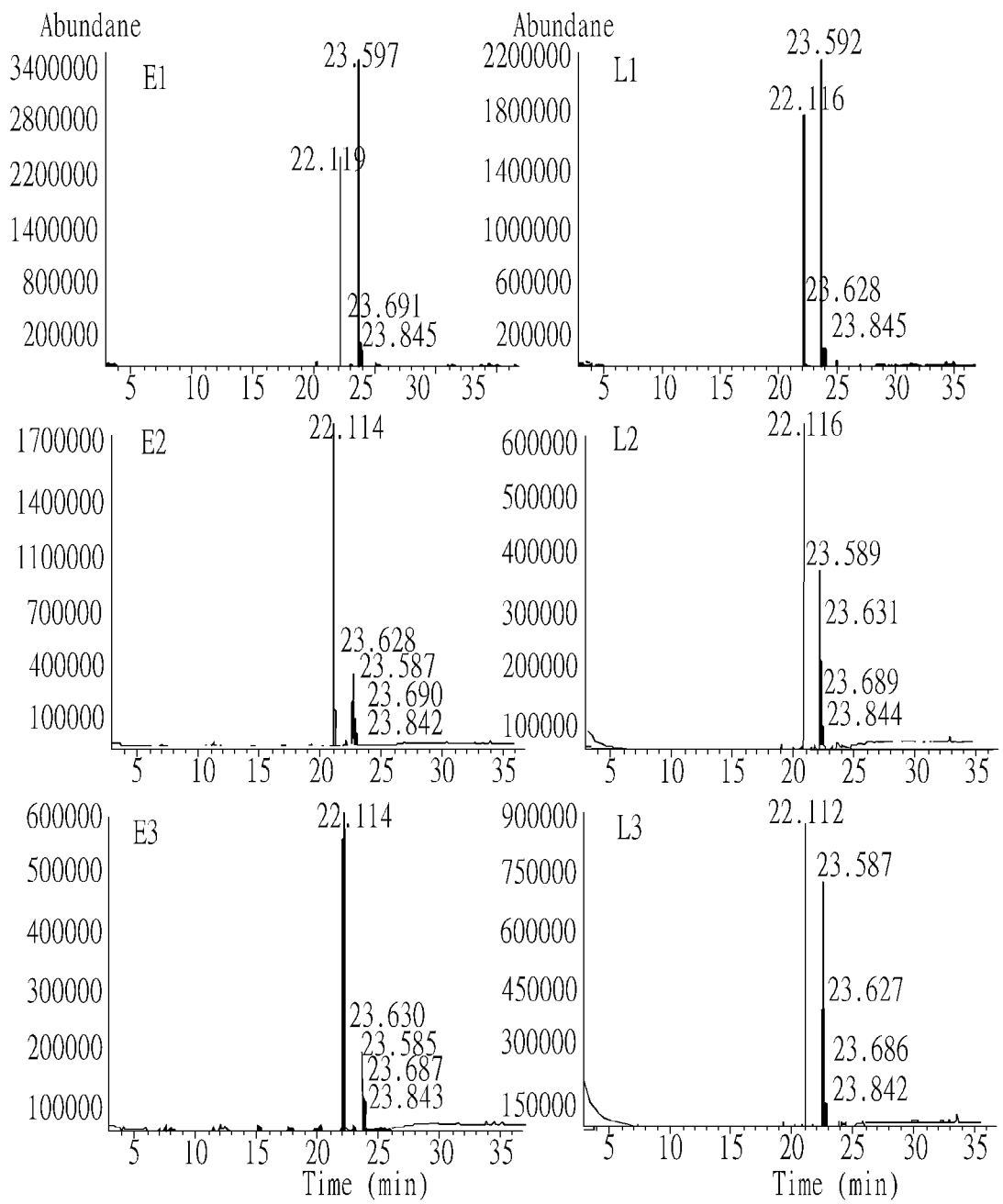
FIG. 8 is of GC-MS spectra for lipid components of individual gintonins E1~E3 and L1~L3.

As shown in Table 3 and FIG. 8, individual gintonins contained palmitic, stearic, oleic and linoleic acids in ester form or free form.

The portions of polyunsaturated fatty acid and linoleic acid in the gintonins E1 and L1 were higher than were saturated fatty acids such as palmitic acid, stearic acid or oleic acid. Palmitic acid was predominant in gintonins E2, E3, L2, and L3.

The content of total lipids in gintonins were about 34.3% for gintonin E1, 45.3% for E2, 38.1% for E3, 36.0% for L1, 29,8% for L2 and 45.2% for L3 as measured by GC, with the highest lipid content detected in gintonin E1.

These results indicate that gintonins of the present invention are novel glycolipoproteins.

TABLE 3

Lipids composition of gintonins

| Lipids | E1 | E2 | E3 | L1 | L2 | L3 |
|---|---|---|---|---|---|---|
| Palmitic acid (16:0), ester form | 29.82 | 57.39 | 56.59 | 36.48 | 41.78 | 39.5 |
| Stearic acid (18:0), ester form | 4.22 | 8.73 | 8.20 | 4.74 | 5.49 | 5.44 |
| Oleicacid (18:1) or oleic acid ester form | 7.08 | 26.06 | 27.52 | 14.32 | 30.04 | 26.64 |
| Linoleic acid (18:2) or linoleic acid ester form | 58.88 | 7.82 | 7.69 | 44.46 | 22.69 | 28.42 |

Measurement Example 1

CaCC Activation in *Xenopus laevis* Oocytes 1-(1). Oocyte Preparation

*Xenopus laevis* frogs were obtained from *Xenopus* I (Ann Arbor, Mich.). Their care and handling were in accordance with the highest standards of institutional guidelines. To isolate oocytes, the frogs were operated on under anesthesia with an aerated solution of 3-aminobenzoic acid ethyl ester. Oocytes were separated by treatment with collagenase and agitation for two hours in a $Ca^{2+}$-free medium containing 82.5 mM NaCl, 2 mM KCl, 1 mM MgCl2, 5 mM HEPES, 2.5 mM sodium pyruvate, 100 units/ml penicillin and 100 μg/ml streptomycin.

Stage V-VI oocytes were collected and stored in ND96 (96 mM NaCl, 2 mM KCl, 1 mM $MgCl_2$, 1.8 mM $CaCl_2$, and 5 mM HEPES, pH 7.5) supplemented with 50 μg/ml gentamicin. This oocyte containing solution was maintained at 18° C. with continuous gentle shaking and was changed every day.

1-(2). Measurement of CaCC

Two-electrode voltage-clamp recordings were obtained from individual oocytes placed in a small Plexiglas net chamber (0.5 ml). Electrophysiological experiments were performed at room temperature using microelectrodes filled with 3 M KCl (resistance of 0.2-0.7 MΩ) and an Oocyte Clamp amplifier (OC-725C; Warner Instrument, Hamden, Conn.), followed by recording CaCC at −80 mV holding potential.

Gintonins were applied to oocytes by bath perfusion (Lee, J. H., Jeong, S. M., Lee, B. H., Noh, H. S., Kim, B. K., Kim, J. I., Rhim, H., Kim, H. C., Kim, K. M., and Nah, S. Y. (2004) *J Biol Chem* 279, 9912-9921).

Measurement Example 2

Measurement of Intracellular Free Calcium ([Ca2+]i) in EAT Cells 2-(1). EAT (Ehrlich Ascites Tumor) Cell Preparation EAT cells were harvested by weekly intraperitoneal transplantation into fresh ICR mice as described by Jørgensen et al. (Jørgensen, N. K., Pedersen, S. F., Hoffmann, E. K. (1999) *Am J Physiol*. 276. C26??C37).

In this regard, ascites fluid was collected into a Hank's solution containing 2.5 U/ml heparin from the mouse peritoneal cavity. In order to isolate EAT cells from RBC, EAT cells were loaded into a centrifugal tube containing 10 and 20% Ficoll solution layers and centrifuged at 1,800 rpm for 2 min. EAT cells thus isolated were suspended at a desired cell density and incubated for 30 min before conducting experiments.

2-(2). Loading of EAT Cells with Fura 2

Treatment of GTP-binding protein coupled receptor agonists in fura 2-AM-loaded mouse EAT cells induces transient increases in $[Ca2+]_i$ (Scott and Melvin, Anal. Biochem. 25, 1656-1660, 1953).

An examination was made to see whether gintonin or individual ginsenosides such as ginsenoside Ra, Rb1, Rb2, Rc and Rg1 exhibit their effects on transient increases in $[Ca2+]_i$ in fura 2-AM-loaded EAT cells. For this, the fura 2-AM loaded cells ($2\sim4\times10^6$/mL) were incubated for 10 min in 1.5 mM $Ca^{2+}$ buffer or $Ca^{2+}$ free buffer, and gintonins or ginsenosides were added to the cells and assayed for their effect on intracellular calcium level in EAT cells. Because of the quantitative limitation of available individual purified gintonins, gintonin E2 was used to study the elevation of [Ca2+]i in mouse EAT cells (Riken BRC Cell Bank, Tsukuba, Japan).

EAT cells ($2\sim4\times10^6$ cells/mL) were mixed with 2 μN Fura 2-AM in $Ca^{2+}$ buffer (pH 7.2) containing NaCl 120 mM, KCl 5 mM, $MgCl_2$ 1 mM, $CaCl_2$ 1.5 mM, glucose 10 mM, and HEPES 25 mM and $Ca^{2+}$ free buffer (pH 7.4) containing NaCl 120 mM, KCl 5 mM, $MgCl_2$ 1 mM, EGTA 0.2 mM, glucose 10 mM, and HEPES 25 mM at 37° C. for 30 min in water bath with shaking according to the Jørgensen method, and washed three times with $Ca^{2-}$ buffer or $Ca^{2+}$ free buffer to remove excess fura-2.

2-(3). Fluorescence Measurement of $[Ca^{2+}]_i$ in Cell Suspensions $[Ca^{2+}]_i$ was estimated in fura 2-loaded cells in suspension using an RF-5300PC intracellular ion measurement system (Shimadzu Corporation, Japan). The fura 2-AM loaded cells were diluted with an experimental medium to a final density of $2\sim4\times10^6$ cells/mL and transferred to polystyrene cuvettes (Elkay Ultra-VU). The cells were stirred using Teflon-coated magnets, and the cuvette housing was thermostatically controlled at 37° C. The excitation wavelengths were alternated between 340 and 380 nm under computer control. Emission was detected at 510 nm. Excitation and emission slit widths were 5 nm. Background correction was performed as described by Jorgensen et al. Digitonin and EGTA were used as concentration adjustment reagents to make a condition in which fura 2 completely combines with and disassociates from $Ca^{2+}$.

2-(4). Estimation of $[Ca^{2+}]_i$ from Fura 2 Measurements

Measurements of 340 nm vs. 380 nm ratio values were converted into $[Ca^{2+}]_i$ values using the formula of Hounsell et al. (Hounsell, E. F., Davies, M. J., and Smith, K. D. (1997) *Protein protocol handbood*, Humanna press, Totawa, 803-804).

$[Ca^{2+}]=K_d\,[(R-R_{min})/(R_{max}-R)](S_{f380}/S_{b380})$ wherein Kd is the effective dissociation constant (224 nM), R is a fluorescence ratio of measurements of fluorescence at 340 nm to at 380 nm, and Rmax and Rmin are R values measured at a saturated concentration with 50 μg/ml digitonin and in a free medium with 20 mM EGTA, respectively. $S_{f380}$ and $S_{b380}$ represent fluorescence intensities at 380 nm in the presence of digitonin and EGTA, respectively, and when these values are represented, the ratio thereof is of maximum and minimum values (Grynkiewicz, G., M. Poenie, and R. Y. Tsien, (1985) *J Biol Chem* 260: 3440-3450).

2-(5). Data Analysis

To obtain the concentration-response curve in the presence of $InsP_6$, the observed peak amplitudes were normalized and plotted and then fitted to the following Hill equation below using Origin software (Northampton, Mass.):

$$y/y_{max}=[A]^n/([A]^n+[EC_{50}]^n),$$

wherein y is the percentage activity at a given concentration of gintonin, $y_{max}$ is the maximal peak current, $EC_{50}$ is the concentration of gintonin producing half-maximum effect of the control response to the gintonin, [A] is the concentration of gintonin, and n is the interaction coefficient. All values are presented as means±S.E. The differences between means of the control and gintonin treatment data were analyzed using an unpaired Student's t-test. A value of p<0.05 was considered statistically significant.

Test Example 1

Effects of Crude and Individual Gintonins on Endogenous CaCC in *Xenopus laevis* Oocytes In order to examine the effect of crude gintonin and individual gintonins on endogenous CaCC activation in *Xenopus laevis* oocytes, holding potentials recorded by the activation of CaCC were measured using the methods described in Measurement Example 1.

Figure 9:
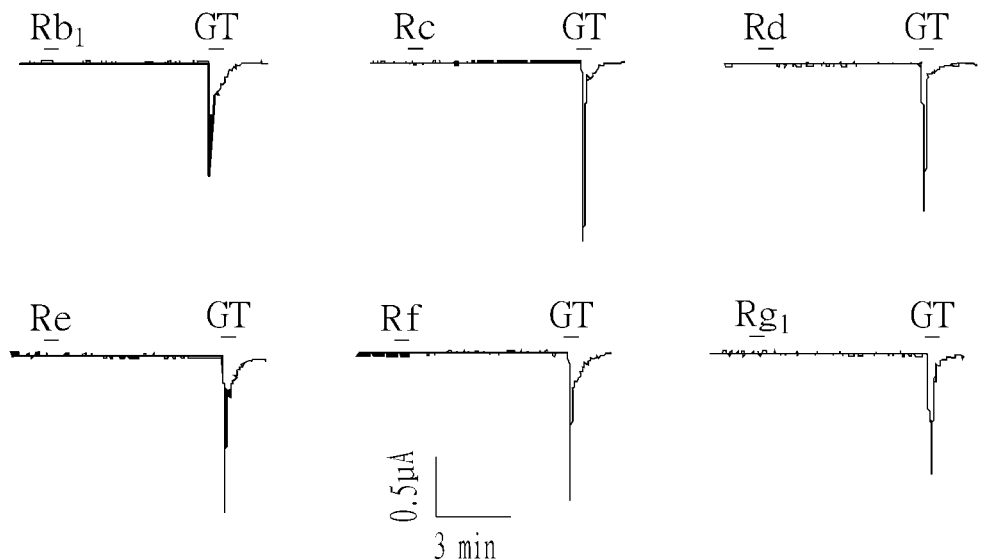
FIG. 9 shows inward Cl⁻ currents of endogenous CaCC in mouse EAT cells upon treatment with gintonins and ginsenoides at −80 mV holding potential (A) and in concentration-dependent manners upon treatment with crude gintonin and individual gintonins (B and C, respectively).
Figure 9:
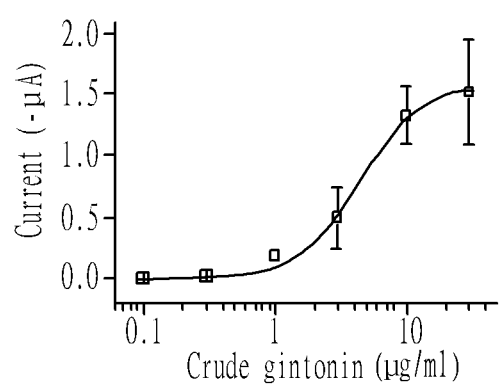
Figure 9:
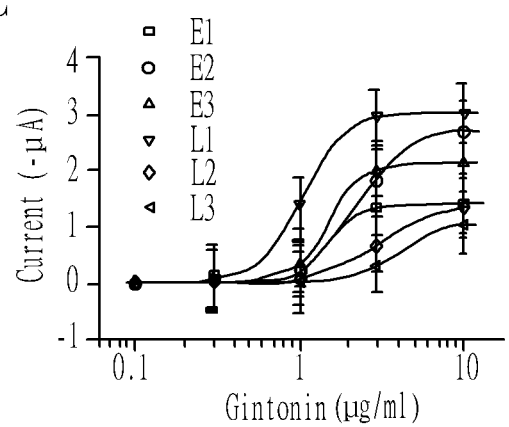

Treatment of crude gintonin induced inward Cl⁻ currents at −80 mV holding potential, with an $ED_{50}$ detected at 4.4±0.5 μg/mL whereas none of ginsenosides had an effect on CaCC activity (see FIGS. 9A and 9B).

In addition, individual gintonins were assayed for their ability to induce CaCC activation in *Xenopus* oocytes. Gintonins E1~E3 and L1 were found to have almost the same degree of effect on CaCC activation while gintonin L2 and L3 induced weaker CaCC activation than the other individual gintonins (see FIG. 9C). The ED50 values were 1.5±0.1 μg/mL for E1, 2.3±0.1 μg/mL for E2, 1.5±0.1 μg/mL for E3, 1.0±0.1 μg/mL for L1, 3.2±0.2 μg/mL for L2, and 4.3±0.2 μg/mL for L3.

Test Example 2

Effect on Intracellular Free Calcium ($[Ca^{2+}]_i$) in Mouse EAT Cells

Measurement was made of intracellular $[Ca^{2-}]_i$ in mouse EAT cells using the methods described in Measurement Example 2. When applied to EAT cells in a suspension, 100 μM of each of individual ginsenosides did not induce any response at all in the cells. In contrast, a transient increase of $[Ca^{2+}]_i$ was detected in the group treated with 100 ng/mL gintonin E2 (see FIG. 10A).

Figure 10:
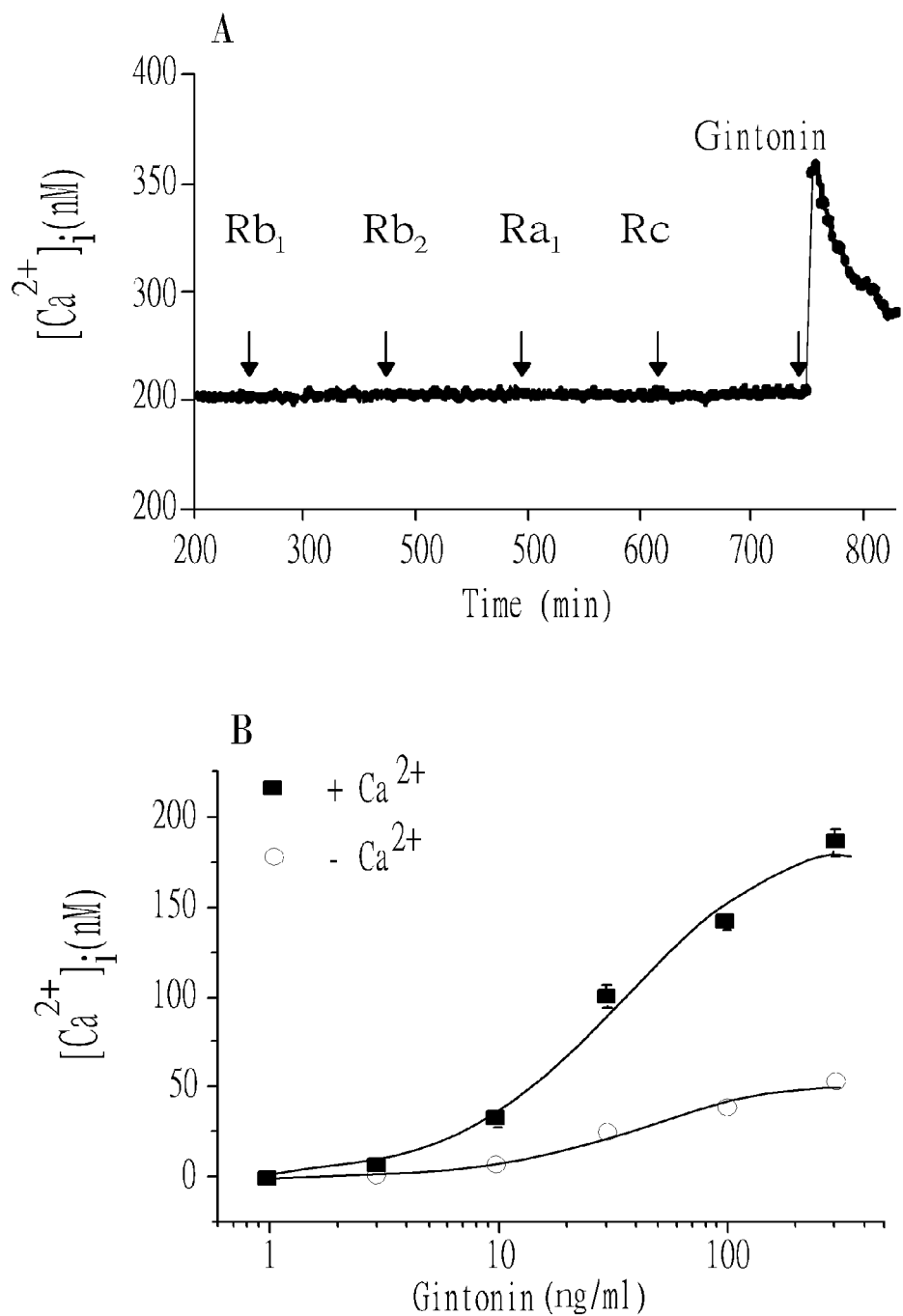
FIG. 10 shows the elevation of intracellular calcium levels in mouse EAT cells when Fura-2 loaded cells are incubated in a $Ca^{2+}$ buffer for a predetermined period of time in the presence of gintonins (A) and in a concentration-dependent manner when Fura-2 cell loaded cells are incubated in either $Ca^{2+}$ buffer or $Ca^{2+}$ free buffer (0.2 mM EGTA) in the presence of gintonins (B).

FIG. 10B also shows that the gintonin E2-induced elevation of $[Ca^{2+}]_i$ was dependent on concentration. Interestingly, the gintonin E2-induced transient elevation of $[Ca^{2+}]_i$ was greatly reduced by the removal of external $Ca^{2+}$ ($Ca^{2+}$-free medium containing 0.2 mM EGTA) (P<0.001, compared to extracellular $Ca^{2+}$), indicating the influx of extracellular $Ca^{2+}$ into cells upon treatment with gintonin. However, treatment of gintonin E2 still increased $[Ca^{2+}]_i$ in a concentration-dependent manner, suggesting that gintonin E2-induced elevation of $[Ca^{2+}]_i$ is likely due to $Ca^{2+}$ release from stored intracellular $Ca^{2+}$ and $Ca^{2+}$ entry from the extracellular side.

The EC50 values were 33.6±8.2 ng/mL and 43.6±14.2 ng/mL (mean±S.E., n=5~6) according to the presence and absence of extracellular $Ca^{2+}$, respectively. These data indicate that it is gintonin not not ginsenoide that causes an increase in $[Ca^{2+}]_i$ in mammal cells.

Test Example 3

Effects of PLC Inhibitor, IP3 Receptor Antagonist, or Ca2+ Chelator on Crude Gintonin-Mediated CaCC Activation and $[Ca^{2+}]_i$ Elevation To elucidate the possible role of phospholipase C (PLC) in the gintonin-mediated signaling pathway for increasing cytoplasmic $[Ca^{2'}]_i$ and CaCC activations, the effects of the active PLC inhibitor, U-73122 and the inactive analog, U-73343 were examined using *Xenopus* oocytes and mouse EAT cells.

Figure 11:
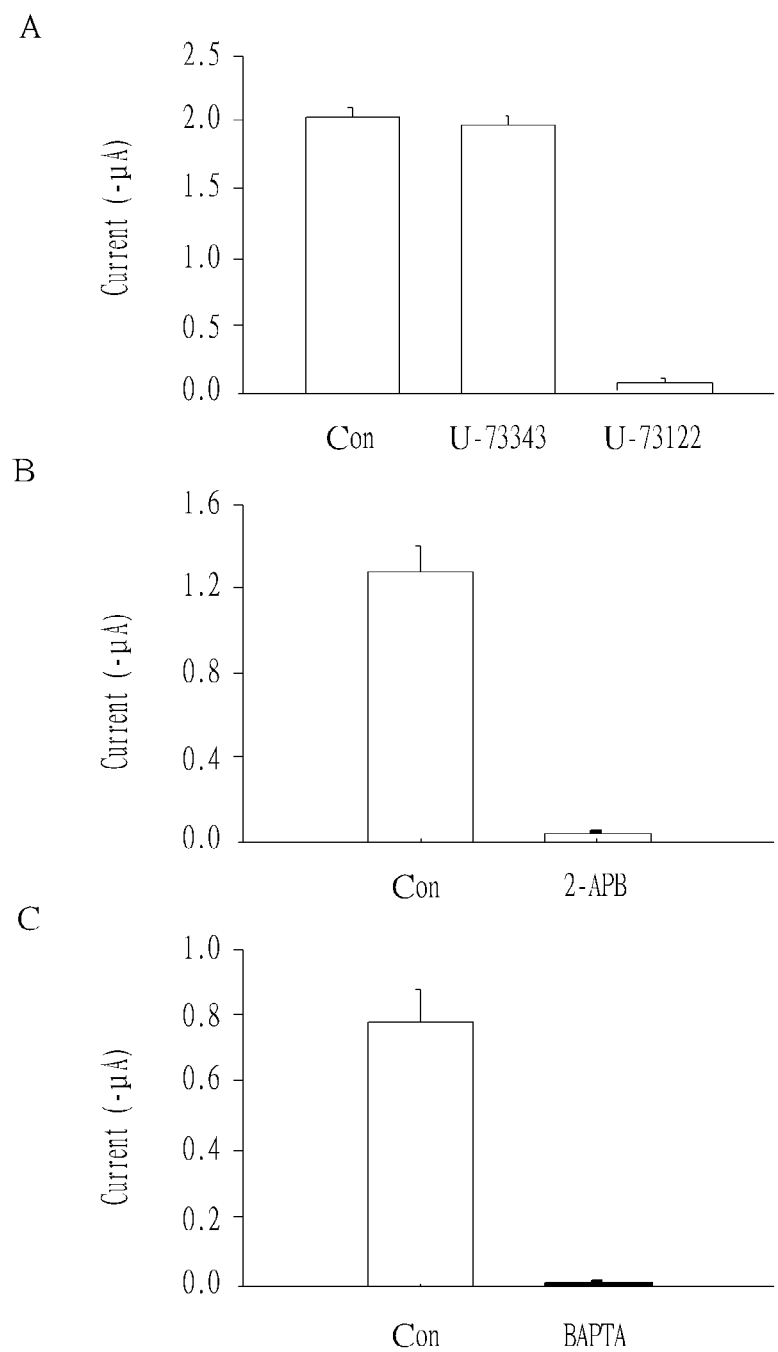
FIG. 11 is of histograms of current amplitudes showing the effects of a PLC inhibitor, an IP3 receptor agonist and a Ca2+ chelator on gintonin-mediated CaCC activation and the elevation of intracellular calcium in mouse EAT cells in which CaCC activation is diminished by the PLC inhibitor (U-73343/U-73122) (A), IP3 receptor agonist (2-APB) (B) and $Ca^{2+}$ chelator (BAPTA-AM) (C).

In *Xenopus* oocytes, crude gintonin-induced CaCC currents in U-73122 were 3.9±0.3% of the control, whereas the current in U-73343 was 97.2±0.2% of the control (see FIG. 11A). These results indicate that crude gintonin-mediated $[Ca^{2'}]_i$ elevation and CaCC activations are mediated by means of PLC activation.

In a next step, an examination was made to see whether intracellular $Ca^{2+}$ release through the IP3 receptor led to gintonin-induced CaCC activation (Grynkiewicz, et al., *J. Biol. Chem.* 260: 3440-3450, 1985; Parekh, A. B. *Pflugers Arch.-Eur. J. Physiol.*, 430, 954-963, 1995; Broad, et al., *J. Biol. Chem.* 276, 15945-15952, 2001).

For this, the effect of the IP3 receptor antagonist, membrane permeable 2-aminoethxydiphenyl borate (2-APB), on gintonin-induced CaCC activation was examined.

As shown in FIG. 11B, the addition of 2-APB almost completely abrogated the inward CaCC currents induced by gintonin (control currents of from 1.3±0.2 to 0.03±0.01 μA, P<0.01). In addition, buffering intracellular free Ca2+ by treatment with membrane permeable 1,2-bis-(2-aminophenoxy)ethane-N,N,N',N'-tetraacetic acid acetoxymethyl ester (BAPTA-AM) (10 μM final) also almost extinguished gintonin-mediated CaCC activation (see FIG. 11C).

Figure 12:
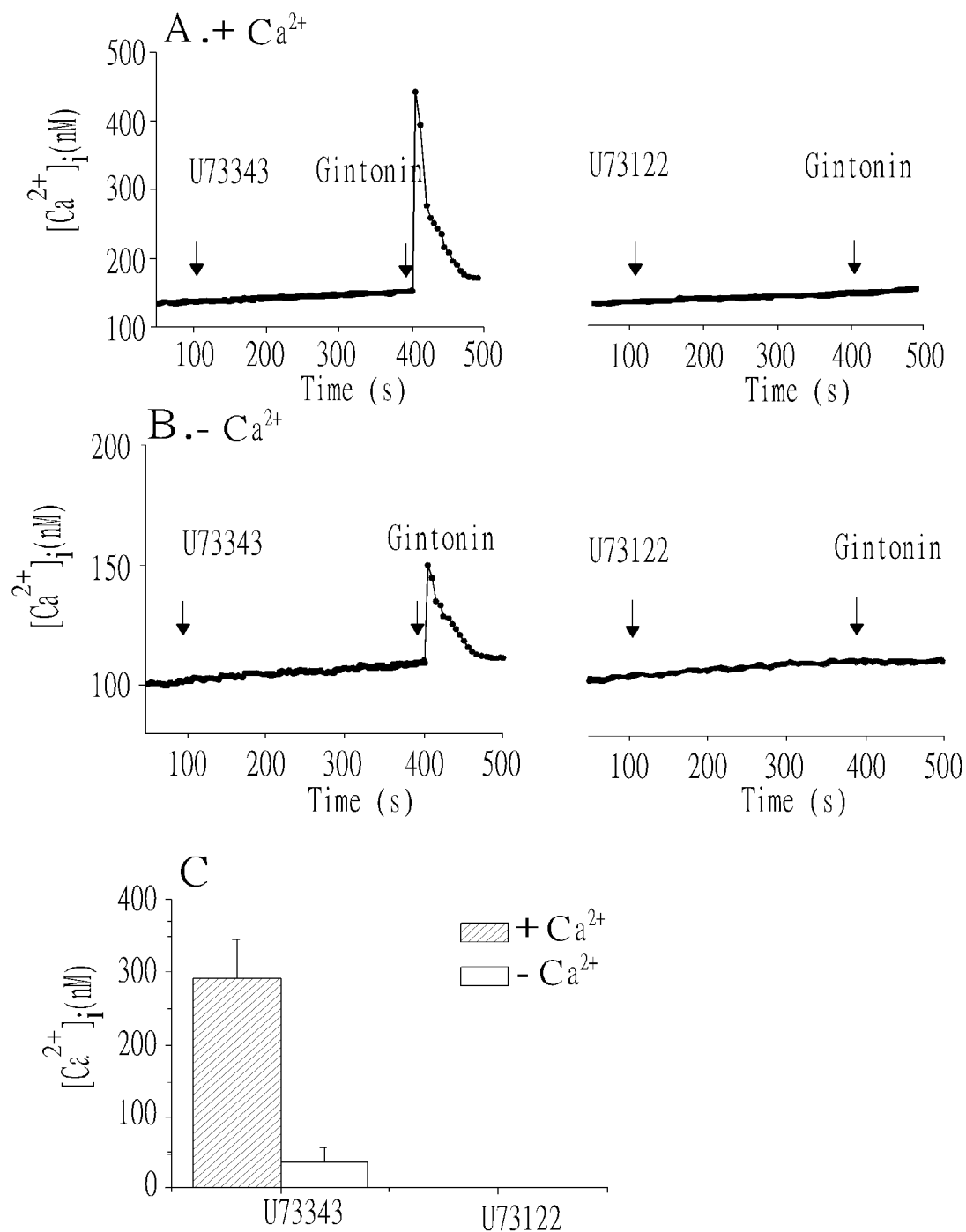
FIG. 12 shows the effect of active or inactive PLC inhibitors on the gintonin-mediated increase of intracellular calcium level in mouse EAT cells in which intracellular calcium level is decreased in Fura-2-loaded EAT cells incubated in Ca2+ buffer (A) and in a concentration-dependent manner in Fura-2-loaded EAT cells cultured in $Ca^{2+}$-free buffer (B).

In mouse EAT cells, the application of U-73122 but not U-73343 was observed to almost abrogate the action of gintonin irrespective of the presence of extracellular $Ca^{2+}$ (see FIG. 12).

These results again demonstrate that gintonin is the main active component of CGSF responsible for the activation of CaCC via the PLC-IP3-$Ca^{2+}$ pathway in *Xenopus* oocytes and mouse EAT cells.

Consequently, gintonins, the novel glycolipoproteins of the present invention, can increase intracellular calcium levels by creating an influx of extracellular calcium so that $Ca^{2+}$ can be utilized as a mediator of intracellular signaling pathways of a variety of physiological and pharmacological actions of ginseng.

Formulation examples for the pharmaceutical composition comprising gintonin according to the present invention are given herein, below, to illustrate yet not to limit the present invention.

Formulation Example 1

Preparation of Tablet

| | |
|---|---|
| Gintonin | 100 mg |
| Lactose | 100 mg |
| Starch | 100 mg |
| Magnesium Stearate | 2 mg |

These ingredients were mixed and prepared into tablets using a typical tabletting method.

Formulation Example 2

Preparation of Powder

| | |
|---|---|
| Gintonin | 100 mg |
| Lactose | 100 mg |
| Talc | 10 mg |

The above ingredients were mixed and loaded into an airtight sac to produce a powder agent.

Formulation Example 3

Preparation of Capsule

| | |
|---|---|
| Gintonin | 100 mg |
| Crystalline Cellulose | 3 mg |
| Lactose | 14.8 mg |
| Magnesium stearate | 0.2 mg |

These ingredients were mixed and loaded into gelatin capsules according to a typical method of producing capsules.

Formulation Example 4

Preparation of Injection

| | |
|---|---|
| Gintonin | 10 mg |
| Sterile Distilled Water for Injection | q.s. |
| pH Adjuster | q.s. |

According to a typical method, the active ingredient, along with the excipient, was dissolved and the solution was loaded into type I ampoules (2 ml).

Formulation Example 5

Preparation of Liquid

| | |
|---|---|
| Gintonin | 1000 mg |
| Isomerized Sugar | 10 g |
| Mannitol | 5 g |
| Purified Water | q.s. |

According to a typically used method, the ingredients were dissolved in purified water and a lemon aromatic was added in a suitable amount to the solution. After complete mixing, the solution was increased in volume to 100 ml with purified water, loaded into brown vials and sterilized to give a liquid preparation.

Formulation Example 6

Preparation of Health Food

| | |
|---|---|
| Gintonin | 1,000 mg |
| Vitamin Mixture | q.s. |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinamide | 1.7 mg |
| Folic acid | 50 μg |
| Calcium Pantothenate | 0.5 mg |
| Mineral Mixture | q.s. |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

This composition of the vitamins and minerals was provided as a preferred example suitable for use in a health food, but the contents may be changed depending on conditions. According to a typical method, these ingredients were mixed and formulated into granules which could be applied to the preparation of health foods.

Formulation Example 7

Preparation of Health Beverage

| | |
|---|---|
| Gintonin | 100 g |
| Vitamin C | 15 g |
| Vitamin E (powder) | 100 g |
| Ferrous lactate | 19.75 g |
| Zinc oxide | 3.5 g |
| Nicotinic acid amide | 3.5 g |
| Vitamin A | 1.0 g |
| Vitamin B1 | 0.13 g |
| Vitamin B2 | 0.15 g |

These ingredients were homogeneously formulated according to a typically used method and the formulation was heated at 85° C. for about 1 hour with stirring, sterilized by filtration, loaded into a 2 L bottle, sealed, and stored in a refrigerator until use.

This composition is provided as a preferred example suitable for use in beverages, but the contents may be changed depending on regional and national factors, such as consumer class, country, etc.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for isolating gintonin comprising:

extracting ginseng with aqueous methanol and then fractionating with a mixture of water and n-butanol to yield a water fraction and a n-butanol fraction;

subjecting the n-butanol fraction to silica gel chromatography and eluting with a mixture of chloromethane, methanol and water to yield eight fractions which are then assayed for $Ca^{2+}$-activated chloride channel activation in xenopus oocytes;

fractionating the seventh fraction which has the highest activity in xenopus oocytes by silica gel chromatography and eluting with a mixture of ethanol, ethylacetate and water to yield two subfractions;

assaying the two subfractions for their ability to induce intracellular calcium release in Ehrlich Ascites Tumor cells and CaCC activation in xenopus oocytes; and dialyzing subfraction two which has a higher activity than subfraction one to induce intracellular calcium release in Ehrlich Ascites Tumor cells and CaCC activation in xenopus oocytes against excess water in a dialysis bag to remove ginsenosides and yield said isolated gintonin.

2. The method of claim 1, further comprising partitioning the isolated gintonin in phosphate buffered saline into two subfractions by anion exchange chromatography and gel filtration chromatography; and subjecting one of the two subfractions to anion exchange chromatography using Tris-HCl and the other subfraction to anion exchange chromatography using phosphate buffered saline in order to separate and yield individual glycolipoproteins E1, E2, E3, L1, L2 and L3.

3. The method of claim 1, wherein the ginseng is selected from the group consisting of red ginseng and white ginseng.

* * * * *